United States Patent
Kesteleyn et al.

(10) Patent No.: US 7,514,427 B2
(45) Date of Patent: Apr. 7, 2009

(54) 1,5,6,-SUBSTITUTED-2-OXO-3-CYANO-1,6A-DIAZA-TETRAHYDRO-FLUORANTHENES AS ANTI-INFLECTIVE AGENTS

(75) Inventors: Bart Rudolf Romanie Kesteleyn, Berlare (BE); Pierre Jean-Marie Raboisson, Sterrebeek (BE); Wim Van De Vreken, Beveren (BE); Maxime Francis Jean-Marie Ghislain Canard, La Hulpe (BE)

(73) Assignee: Tibotec Pharmaceuticals, Ltd. (IE)

( * ) Notice: Subject to any disclaimer, the term of this patent is extended or adjusted under 35 U.S.C. 154(b) by 0 days.

(21) Appl. No.: 11/722,951

(22) PCT Filed: Jan. 10, 2006

(86) PCT No.: PCT/EP2006/050106

§ 371 (c)(1),
(2), (4) Date: Jun. 27, 2007

(87) PCT Pub. No.: WO2006/072636

PCT Pub. Date: Jul. 13, 2006

(65) Prior Publication Data

US 2008/0167296 A1    Jul. 10, 2008

Related U.S. Application Data

(60) Provisional application No. 60/684,706, filed on May 26, 2005.

(30) Foreign Application Priority Data

Jan. 10, 2005    (EP)    ................... 05100092

(51) Int. Cl.
C07D 498/22    (2006.01)
C07D 487/22    (2006.01)
A61K 31/5365    (2006.01)
A61K 31/4985    (2006.01)

(52) U.S. Cl. ................. 514/224.5; 514/229.5; 514/250; 544/14; 544/99; 544/343

(58) Field of Classification Search ................... 544/14, 544/99, 343; 514/224.5, 229.5, 250
See application file for complete search history.

(56) References Cited

FOREIGN PATENT DOCUMENTS

WO    WO 2004/046143 A1    6/2004

OTHER PUBLICATIONS

International Search Report dated Aug. 4, 2006 for related International Application No. PCT/EP2006/050106.

*Primary Examiner*—Kahsay T Habte
(74) *Attorney, Agent, or Firm*—Laura A. Donnelly

(57) ABSTRACT

HIV inhibitory compounds of formula:

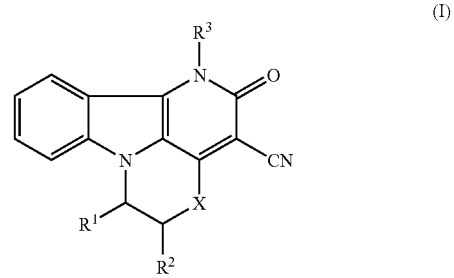

(I)

salts and stereoisomers thereof, wherein
$R^1$ and $R^2$ are hydrogen or optionally substituted $C_{1-10}$alkyl;
$R^3$ is

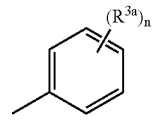

n is 1, 2 or 3;
$R^{3a}$ is nitro, cyano, amino, halo, hydroxy, $C_{1-4}$alkyloxy, hydroxycarbonyl, aminocarbonyl, $C_{1-4}$alkyloxycarbonyl, mono- or di($C_{1-4}$alkyl)aminocarbonyl, $C_{1-4}$alkylcarbonyl, methanimidamidyl, mono- or di($C_{1-4}$alkyl) methanimidamidyl, N-hydroxy-methanimidamidyl or Het; or
$R^3$ is a monocyclic or bicyclic aromatic heterocyclic ring system, wherein one, two, three or four ring members are nitrogen, oxygen and sulfur, and wherein the remaining ring members are carbon atoms; and wherein each of said heterocyclic ring systems may optionally be substituted;
X is $-NR^7-$, $-O-$ or $-S-$;
pharmaceutical compositions containing these compounds, methods for preparing these compounds and compositions.

11 Claims, No Drawings

1,5,6,-SUBSTITUTED-2-OXO-3-CYANO-1,6A-DIAZA-TETRAHYDRO-FLUORANTHENES AS ANTI-INFLECTIVE AGENTS

CROSS REFERENCE TO RELATED APPLICATIONS

This application is a national stage application of Patent Application No. PCT/EP2006/050106, filed Jan. 10, 2006, which application claims priority from EPO patent application 05100092.5, filed Jan. 10, 2005, and U.S. Provisional Application No. 60/684,706, filed May 26, 2005, all of which are hereby incorporated by reference in their entirety.

This invention relates to substituted 2-oxo-3-cyano-1,6a-diaza-tetrahydro-fluoranthenes, the use thereof as anti-infective agents, and to pharmaceutical compositions containing these compounds.

The human immunodeficiency virus (HIV) is the aetiological agent of the acquired immunodeficiency syndrome (AIDS) of which two distinct types have been identified, i.e. HIV-1 and HIV-2. Hereinafter, the term HIV is used to generically denote both these types. AIDS patients are currently treated with a variety of agents such as HIV reverse transcriptase inhibitors (RTIs), HIV protease inhibitors (PIs) and entry inhibitors. There exist several classes of RTIs, namely nucleoside reverse transcriptase inhibitors (NRTIs) such as zidovudine, didanosine, zalcibatine, stavudine, abacavir and lamivudine, non-nucleoside reverse transcriptase inhibitors (NNRTIs) such as nevirapine, delavirdine and efavirenz, and nucleotide reverse transcriptase inhibitors (NtRTIs) such as tenofovir.

HIV inhibitors are usually administered in combinations comprising two or more compounds of the above classes of drugs. Despite the fact that these antiretrovirals have been applied succesfully, they have a common limitation, namely, the targeted enzymes in the HIV virus are able to mutate in such a way that any of the known drugs become less effective, or even ineffective against these mutant HIV viruses. Or, in other words, the HIV virus creates an ever-increasing resistance against any available drugs and the emergence of this resistance is a major cause of therapy failure. Moreover, it has been shown that resistant virus is carried over to newly infected individuals, resulting in severely limited therapy options for these drug-naive patients. The emergence of resistance moreover forces the physician to prescribe higher doses and/or more frequent administrations of the drug to boost plasma levels in order to regain effectivity. This contributes to the so-called 'pill burden' which is a major cause of non-compliance with the prescribed therapy.

All RTIs give rise to the emergence of resistance and especially the currently used NNRTIs are sensitive to this phenomenon due to mutations at amino acids that surround the NNRTI-binding site. Hence there is a need for new types of HIV inhibitors that target HIV reverse transcriptase, which are able to delay the emergence of resistance and are effective against a broad spectrum of mutants of the HIV virus.

WO-02/055520 and WO-02/059123 disclose benzoylalkylindolepyridinium compounds as antiviral compounds. Ryabova et al. disclose the synthesis of certain benzoylalkylindolepyridinium compounds (Russian Chem. Bull. 2001, 50(8), 1449-1456) (Chem. Heterocycl. Compd. (Engl. Translat.) 36; 3; 2000; 301-306; Khim. Geterotsikl. Soedin.; RU; 3; 2000; 362-367). WO-04/046143 discloses certain substituted 1-phenyl-1,5-dihydro-pyrido[3,2-b]indol-2-ones as anti-HIV compounds.

The present invention provides a new series of compounds that are structurally different from the compounds of the prior art, and show activity not only against wild type HIV virus but also against a variety of mutant HIV viruses including mutant HIV viruses showing resistance against currently available reverse transcriptase inhibitors.

Thus in one aspect, the present invention concerns substituted 2-oxo-3-cyano-1,6a-diaza-tetrahydro-fluoranthenes of formula (I):

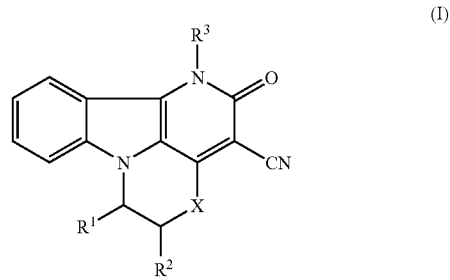

the salts and stereoisomeric forms thereof, wherein
$R^1$ and $R^2$ are each, independently, hydrogen or $C_{1-10}$alkyl, which may be optionally substituted with a substituent selected from hydroxy, cyano, $NR^4R^5$, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $(R^4)(R^5)$N-carbonyl, $C_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-($C_{1-4}$alkyl)-piperazin-1-ylcarbonyl, morpholin-1-yl-carbonyl, thiomorpholin-1-ylcarbonyl, 1-oxothiomorpholin-1-ylcarbonyl and 1,1-dioxo-thiomorpholin-1-ylcarbonyl;

$R^3$ is a radical of formula

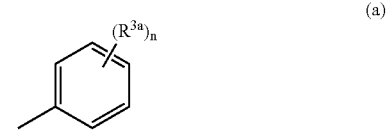

wherein n is 1, 2 or 3;
$R^{3a}$ is nitro, cyano, amino, halo, hydroxy, $C_{1-4}$alkyloxy, hydroxycarbonyl, aminocarbonyl, $C_{1-4}$alkyloxycarbonyl, mono- or di($C_{1-4}$alkyl)aminocarbonyl, $C_{1-4}$alkylcarbonyl, methanimidamidyl, mono- or di($C_{1-4}$alkyl)methanimidamidyl, N-hydroxy-methanimidamidyl or Het; or
$R^3$ is a monocyclic or bicyclic aromatic heterocyclic ring system, wherein one, two, three or four ring members are heteroatoms each independently selected from nitrogen, oxygen and sulfur, and wherein the remaining ring members are carbon atoms; and wherein each of said heterocyclic ring systems may optionally be substituted with one, two, three, four or five substituents each independently selected from halo, cyano, nitro, $C_{1-6}$alkyl, hydroxy$C_{1-6}$alkyl, $C_{1-4}$alkoxy$C_{1-6}$alkyl, $(R^{5a})(R^{5b})$N—$C_{1-4}$alkyl, polyhalo$C_{1-6}$alkyl, $C_{3-7}$cycloalkyl, aryl$C_{1-6}$alkyl, formyl, $C_{1-6}$alkylcarbonyl, a radical —COOR$^6$, $(R^{5a})(R^{5b})$N-carbonyl, $(R^{5a})(R^{5b})$N-sulfonyl, hydroxy, $C_{1-6}$alkyloxy, aryl$C_{1-6}$alkyloxy, polyhalo$C_{1-6}$alkyloxy, formyloxy, $C_{1-6}$alkylcarbonyloxy, aryloxy, a radical $(R^{5a})(R^{5b})$N—, formylamino, $C_{1-6}$alkylcarbonylamino, $C_{1-6}$alkyloxycarbonylamino, $C_{1-6}$alkylsulfonylamino, mercapto, $C_{1-6}$alkylthio, arylthio, aryl$C_{1-6}$alkylthio, $C_{1-6}$alkylsulfinyl, $C_{1-6}$alkylsulfonyl, aryl, —CH(=N—O—$R^{5a}$), and —C(=NH)—NH—$R^{5a}$;

X is —$NR^7$—, —O— or —S—;

$R^4$ and $R^5$ each independently are hydrogen, $C_{1-6}$alkyl or $C_{1-6}$alkyl substituted with a substituent selected from amino, mono- or di-($C_{1-4}$alkyl)amino, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl and 1,1-dioxo-thiomorpholinyl;

each $R^{5a}$, $R^{5b}$ independently is hydrogen, $C_{1-4}$alkyl or aryl$C_{1-4}$alkyl;

$R^6$ is hydrogen, $C_{1-4}$alkyl or aryl$C_{1-4}$alkyl;

$R^7$ is hydrogen, $C_{1-6}$alkyl, optionally substituted with aryl, $(R^4)(R^5)$N—, pyrrolidinyl, piperidinyl, homopiperidinyl, piperazinyl, 4-($C_{1-4}$alkyl)-piperazinyl, morpholinyl, thiomorpholinyl, 1-oxothiomorpholinyl, or with 1,1-dioxothiomorpholinyl;

each aryl independently is phenyl optionally substituted with 1, 2 or 3 substituents each independently selected from $C_{1-6}$alkyl, $C_{1-4}$alkoxy, halo, hydroxy, amino, trifluoromethyl, cyano, nitro, hydroxy$C_{1-6}$alkyl, cyano$C_{1-6}$alkyl, mono- or di($C_{1-4}$alkyl)amino, amino$C_{1-4}$alkyl, mono- or di($C_{1-4}$alkyl)amino$C_{1-4}$alkyl;

Het is a 5- or 6-membered ring system wherein one, two, three or four ring members are heteroatoms each individually and independently selected from nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from $C_{1-4}$alkyl, $C_{2-6}$alkenyl, $C_{3-7}$cycloalkyl, hydroxy, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino$C_{3-6}$alkenyl, mono- or di($C_{1-4}$alkyl)amino$C_{3-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, and thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl.

The term "$C_{1-4}$alkyl" as a group or part of a group defines straight and branched chained saturated hydrocarbon radicals having from 1 to 4 carbon atoms, such as, for example, methyl, ethyl, propyl, butyl, 2-methyl-propyl and the like. The term "$C_{1-6}$alkyl" as a group or part of a group defines straight and branched chained saturated hydrocarbon radicals having from 1 to 6 carbon atoms such as, for example, the groups defined for $C_{1-4}$alkyl and pentyl, hexyl, 2-methylbutyl, 3-methylpentyl and the like. Of interest amongst $C_{1-6}$alkyl are the $C_{1-4}$alkyl radicals. The term "$C_{1-10}$alkyl" as a group or part of a group defines straight and branched chained saturated hydrocarbon radicals having from 1 to 10 carbon atoms such as, for example, the groups defined for $C_{1-6}$alkyl and heptyl, octyl, nonyl, decyl and the like. Of interest amongst $C_{1-10}$alkyl are the $C_{1-6}$alkyl radicals.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Preferred are $C_{2-6}$alkenyls having one double bond. Of interest amongst $C_{2-6}$alkenyl radicals are the $C_{2-4}$alkyl radicals. The term "$C_{3-6}$alkenyl" is as $C_{2-6}$alkenyl but is limited to unsaturated hydrocarbon radicals having from 3 to 6 carbon atoms. In the instances where a $C_{3-6}$alkenyl is linked to a heteroatom, the carbon atom linked to the heteroatom by preference is saturated.

The term "$C_{3-7}$cycloalkyl" is generic to cyclopropyl, cyclobutyl, cyclopentyl, cyclohexyl and cycloheptyl.

The term "halo" is generic to fluoro, chloro, bromo or iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

The term methanimidamidyl is the radical name for $H_2N$—C(=NH)— following the Chemical Abstracts Nomenclature (CAS), which radical can also be referred to as 'amidine'. Likewise N-hydroxy-methanimidamidyl is the CAS radical name for $H_2N$—C(=N—OH)— or its tautomer HN=C(—NH—OH)—, which radical can also be referred to as 'hydroxyamidine'.

In particular, Het is a 5-membered ring system as specified above, and more in particular Het is a 5-membered ring system wherein the ring system contains one oxygen, sulfur or nitrogen, and optionally one, two or three further nitrogen atoms, and wherein the remaining ring members are carbon atoms; optionally substituted with the Het substituents specified above in the definition of the compounds of formula (I) or any subgroup thereof.

Examples of Het rings are furanyl, thienyl, pyrrolyl, oxazolyl, thiazolyl, imidazolyl, isoxazolyl, isothiazolyl, pyrazolyl, oxadiazolyl, thiadiazolyl, triazolyl, and tetrazolyl.

$R^3$ is a monocyclic or bicyclic aromatic heterocyclic ring system as specified above. In particular, $R^3$ may be a monocyclic or bicyclic aromatic heterocyclic ring system as specified above wherein the ring system contains one oxygen, sulfur or nitrogen, and optionally one, two or three further nitrogen atoms and wherein the remaining ring members are carbon atoms; optionally substituted with the substituents specified above in the definition of the compounds of formula (I) or any subgroup thereof.

Examples of $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzo0thienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolo-pyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolo-pyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolo-triazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, and phenoxazinyl; optionally substituted with the substituents specified above in the definition of the compounds of formula (I) or any subgroup thereof.

Particular examples of $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, and phenoxazinyl; optionally substituted with the substituents specified above in the definition of the compounds of formula (I) or any subgroup thereof.

Particularly interesting $R^3$ rings are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuiryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, and quinazolinyl; optionally substituted with the substituents specified above in the definition of the compounds of formula (I) or any subgroup thereof.

It should be noted that different isomers of the various heterocycles may exist within the definitions as used throughout this specification and claims. For example, oxadiazolyl may be 1,2,4-oxadiazolyl, 1,3,4-oxadiazolyl, or 1,2,3-oxadiazolyl; likewise for thiadiazolyl which may be 1,2,4-thiadiazolyl, 1,3,4-thiadiazolyl, or 1,2,3-thiadiazolyl; similarly, pyrrolyl may be 1H-pyrrolyl, or 2H-pyrrolyl.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

When any variable (e.g. halogen or $C_{1-4}$alkyl) occurs more than one time in any constituent, each definition is independent.

The term "compounds of formula (I)", or any similar terms such as "compounds of the invention" and the like, is meant to also comprise any prodrugs that the compounds of formula (I) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, $8^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Akanoyl esters for example are any $C_{1-30}$akanoyl esters, in particular $C_{8-30}$alkanoyl esters, more in particular $C_{10-24}$ alkanoyl esters, further in particular $C_{16-20}$alkanoyl esters, wherein the alkyl part may have one or more double bonds. Examples of alkanoyl esters are decanoate, palmitate and stearate.

The term "compounds of formula (I)", or any similar terms such as "compounds of the invention" and the like, is meant to also comprise any metabolites that are formed in vivo upon administration of the drug. Some examples of metabolites in accordance with the invention include, but are not limited to, (a) where the compound of formula (I) contains a methyl group, a hydroxymethyl derivative thereof; (b) where the compound of formula (I) contains an alkoxy group, an hydroxy derivative thereof; (c) where the compound of formula (I) contains a tertiary amino group, a secondary amino derivative thereof; (d) where the compound of formula (I) contains a secondary amino group, a primary derivative thereof; (e) where the compound of formula (I) contains a phenyl moiety, a phenol derivative thereof; and (f) where the compound of formula (I) contains an amide group, a carboxylic acid derivative thereof.

The term "compounds of formula (I)", or any similar terms such as "compounds of the invention" and the like, is meant to also comprise any N-oxide forms of the compounds of formula (I), which are compounds of formula (I) wherein one or several nitrogen atoms are oxidized to the N-oxide form.

For therapeutic use, the salts of the compounds of formula (I) are those wherein the counter-ion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula (I) containing an acidic proton may also be converted into their non-toxic metal or amine addition base salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The present compounds may also exist in their tautomeric forms. Such forms, although not explicitly indicated in the formulae in this description and claims, are intended to be included within the scope of the present invention. For example, within the definition of Het, an 1,2,4-oxadiazole may be substituted with hydroxy or mercapto in the 5-position, thus being in equilibrium with its respective tautomeric form as depicted below.

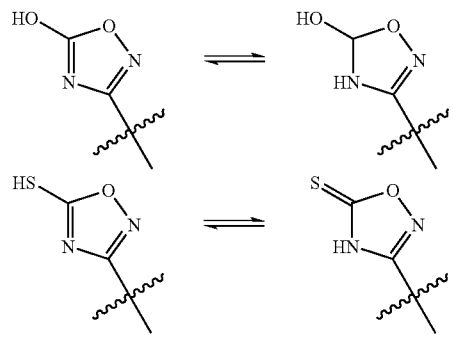

The term "stereochemically isomeric forms" as used herein, defines all possible compounds made up of the same atoms bonded by the same sequence of bonds but having different three-dimensional structures, which are not interchangeable, which the compounds of the present invention may possess. Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention, both in pure form or in a mixture with each other are intended to be embraced within the scope of the present invention, including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalant terms, are meant to include the compounds of general formula (I), or subgroups of the compounds of general formula (I), as well as their N-oxides, salts, stereoisomers, prodrugs, esters and metabolites, in particular their salts and stereoisomers.

Embodiments of the present invention are those compounds of formula (I) or any of the subgroups of compounds of formula (I) wherein
(1) n in $R^{3a}$ is 1 or 2; or
(1-a) n in $R^{3a}$ is 1.

Further embodiments of the present invention are those compounds of formula (I) or any of the subgroups of compounds of formula (I) wherein
(2) $R^1$ is hydrogen or $C_{1-10}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $(R^4)(R^5)$N-carbonyl, $C_{1-4}$alkyloxycarbonyl;
(2-a) $R^1$ is hydrogen or $C_{1-6}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, aryl, furanyl, thienyl, pyrrolyl, oxazolyl, thiazolyl, imidazolyl, triazolyl, pyridyl, pyrimidinyl, pyrazinyl, hydroxycarbonyl, $C_{1-4}$alkylcarbonyl, $(R^4)(R^5)$N-carbonyl, $C_{1-4}$alkyloxycarbonyl;
(2-b) $R^1$ is hydrogen or $C_{1-6}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, hydroxycarbonyl, $(R^4)(R^5)$N-carbonyl;
(2-c) $R^1$ is hydrogen or $C_{1-6}$alkyl substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl;
(2-d) $R^1$ is hydrogen or $C_{1-6}$alkyl substituted with hydroxy, —$NR^4R^5$, pyrrolidinyl, piperidinyl;
(2-e) $R^1$ is hydrogen.

Further embodiments of the present invention are those compounds of formula (I) or any of the subgroups of compounds of formula (I) wherein
(3) $R^2$ is hydrogen or $C_{1-10}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, $C_{1-4}$alkylcarbonyl, $(R^4)(R^5)$N-carbonyl, $C_{1-4}$alkyloxycarbonyl;
(3-a) $R^2$ is hydrogen or $C_{1-6}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, aryl, furanyl, thienyl, pyrrolyl, oxazolyl, thiazolyl, imidazolyl, triazolyl, pyridyl, pyrimidinyl, pyrazinyl, hydroxycarbonyl, $C_{1-4}$alkylcarbonyl, $(R^4)(R^5)$N-carbonyl, $C_{1-4}$alkyloxycarbonyl;
(3-b) $R^2$ is hydrogen or $C_{1-6}$alkyl optionally substituted with hydroxy, cyano, —$NR^4R^5$, pyrrolidinyl, piperidinyl, homopiperidinyl, piperazinyl, 4-($C_{1-4}$alkyl)-piperazinyl, morpholinyl; thiomorpholinyl, 1-oxothiomorpholinyl, 1,1-dioxo-thiomorpholinyl, hydroxycarbonyl, $(R^4)(R^5)$N-carbonyl;
(3-c) $R^2$ is hydrogen or $C_{1-6}$alkyl substituted with hydroxy, cyano, —$NR^4R^5$, pyrrolidinyl, piperidinyl, homopiperidinyl, piperazinyl, 4-($C_{1-4}$alkyl)-piperazinyl, morpholinyl or with thiomorpholinyl;
(3-d) $R^2$ is hydrogen or $C_{1-6}$alkyl substituted with hydroxy, —$NR^4R^5$, pyrrolidinyl, piperidinyl or with morpholinyl;
(3-e) $R^2$ is hydrogen, $C_{1-6}$alkyl substituted with hydroxy, di-$C_{1-4}$alkylamino or with pyrrolidinyl;
(3-f) $R^2$ is hydrogen.

Further embodiments of the present invention are those compounds of formula (I) or any of the subgroups of compounds of formula (I) wherein
(4) X is —O—, —$NR^7$—;
(4-a) X is —$NR^7$—;
(4-b) X is —O—.

Further embodiments of the present invention are those compounds of formula (I) or any of the subgroups of compounds of formula (I) wherein
(5) $R^3$ is phenyl optionally substituted with one or two $R^3a$ radicals selected from nitro, cyano, amino, halo, hydroxy, $C_{1-4}$alkyloxy, hydroxycarbonyl, aminocarbonyl, mono- or di($C_{1-4}$alkyl)aminocarbonyl, $C_{1-4}$alkyloxycarbonyl, $C_{1-4}$alkylcarbonyl, mono- or di($C_{1-4}$alkyl)methanimidamidyl, N-hydroxy-methanimidamidyl or Het; or
$R^3$ is a monocyclic or bicyclic aromatic heterocyclic ring system wherein the ring system contains one oxygen, sulfur or nitrogen, and optionally one, two or three further nitrogen atoms and wherein the remaining ring members are carbon atoms; optionally substituted with one, two, three, four or five substituents each independently selected from the substituents nitro, cyano, amino, halo, hydroxy, $C_{1-4}$alkyloxy, hydroxycarbonyl, aminocarbonyl, mono- or di($C_{1-4}$alkyl)aminocarbonyl, $C_{1-4}$alkyloxycarbonyl, $C_{1-4}$alkylcarbonyl, —CH(=N—O—$R^{5a}$), or —C(=NH)—NH—$R^{5a}$;
(5-a) $R^3$ is phenyl substituted with one or two $R^{3a}$ radicals selected from nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl or Het; or
$R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, or phenoxazinyl; optionally substituted with one, two, three, or four substituents each independently selected from nitro, cyano, halo, $C_{1-4}$alkyloxy, hydroxycarbonyl, or aminocarbonyl;

(5-b) $R^3$ is phenyl substituted with one or two radicals selected from nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, wherein each of said furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl may optionally be substituted with one or two substituents selected from the group consisting of $C_{1-4}$alkyl, $C_{2-6}$alkenyl, $C_{3-7}$cycloalkyl, hydroxy, $C_{1-4}$alkoxy, amino, cyano, trifluoromethyl, hydroxyl-$C_{1-4}$alkyl, cyano$C_{1-4}$alkyl, mono- or di($C_{1-4}$alkyl)amino, amino$C_{1-4}$alkyl, mono- or di($C_{1-4}$alkyl)amino$C_{1-4}$alkyl, aryl$C_{1-4}$alkyl, amino-$C_{3-6}$alkenyl, mono- or di($C_{1-4}$alkyl) amino$C_{3-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl, oxo, or thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl; or $R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzo-thienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolo-pyrimidinyl, thiadiazolopyrimidinyl, triazolopyrimidinyl, carbazolyl, acridinyl, phenothiazinyl, or phenoxazinyl; optionally substituted with one, two, or three substituents each independently selected from halo, cyano, nitro, $C_{1-6}$alkyl, hydroxy$C_{1-6}$alkyl, $C_{1-4}$alkoxy$C_{1-6}$alkyl, $(R^{5a})(R^{5b})N$—$C_{1-4}$alkyl, $CF_3$, $C_{3-7}$cycloalkyl, formyl, $C_{1-6}$alkylcarbonyl, a radical —$COOR^6$, $(R^{5a})(R^{5b})$ N-carbonyl, hydroxy, $C_{1-6}$alkyloxy, a radical $(R^{5a})(R^{5b})N$—, mercapto, $C_{1-6}$alkylthio, $C_{1-6}$alkylsulfonyl, aryl, —CH(=N—O—$R^{5a}$), or —C(=NH)—NH—$R^{5a}$;

(5-c) $R^3$ is phenyl substituted with one or two radicals selected from nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, oxadiazolyl, thienyl, thiazolyl, furanyl, and isoxazolyl, wherein each of said oxadiazolyl, thienyl, thiazolyl, furanyl, isoxazolyl may optionally be substituted with $C_{1-4}$alkyl; or $R^3$ is pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, or quinazolinyl; optionally substituted with one, two, or three substituents each independently selected from halo, cyano, nitro, $C_{1-6}$alkyl, hydroxy$C_{1-6}$alkyl, $C_{1-4}$alkoxy$C_{1-6}$alkyl, $C_{3-7}$cycloalkyl, $C_{1-6}$alkylcarbonyl, a radical —$COOR^6$, $(R^{5a})(R^{5b})$N-carbonyl, hydroxy, $C_{1-6}$alkyloxy, a radical $(R^{5a})(R^{5b})N$—, mercapto, $C_{1-6}$alkylthio, or $C_{1-6}$alkylsulfonyl;

(5-d) $R^3$ is phenyl substituted with one or two radicals selected from nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, oxadiazolyl, isoxazolyl, thienyl, pyrrolyl, triazolyl, thiazolyl, furanyl, isoxazolyl, and tetrazolyl, wherein each of said oxadiazolyl, isoxazolyl, thienyl, pyrrolyl, triazolyl, thiazolyl, furanyl, or isoxazolyl may optionally be substituted with $C_{1-4}$alkyl;

(5-e) $R^3$ is phenyl substituted with one or two radicals selected from nitro, cyano, halo, $C_{1-4}$alkyloxy, hydroxycarbonyl, aminocarbonyl, mono- or di($C_{1-4}$alkyl)methanimidamidyl, N-hydroxy-methanimidamidyl, oxadiazolyl, isoxazolyl, thienyl, pyrrolyl, triazolyl, thiazolyl, furanyl, isoxazolyl or tetrazolyl, wherein each of said oxadiazolyl, isoxazolyl, thienyl, pyrrolyl, triazolyl, thiazolyl, furanyl, or isoxazolyl may optionally be substituted with $C_{1-4}$alkyl;

(5-f) $R^3$ is phenyl substituted with nitro, cyano, halo, $C_{1-4}$alkyloxy, hydroxycarbonyl, aminocarbonyl;

(5-g) $R^3$ is phenyl substituted with nitro; or (5-h) the $R^{3a}$ group on the phenyl ring is in the para position vis-à-vis the nitrogen atom in the fused pyridine moiety.

Further embodiments of the present invention are those compounds of formula (I) or any of the subgroups of compounds of formula (I) wherein each $R^4$ or $R^5$ independently is hydrogen or $C_{1-4}$alkyl.

Other embodiments of the present invention are those compounds of formula (I) or any of the subgroups of compounds of formula (I) wherein each $R^{5a}$ or $R^{5b}$ independently is hydrogen or $C_{1-4}$alkyl.

Other embodiments of the present invention are those compounds of formula (I) or any of the subgroups of compounds of formula (I) wherein $R^6$ is hydrogen or $C_{1-4}$alkyl.

Other embodiments of the present invention are those compounds of formula (I) or any of the subgroups of compounds of formula (I) wherein (6) $R^7$ is hydrogen, $C_{1-6}$alkyl optionally substituted with aryl or with $(R^4)(R^5)N$—;

(6-a) $R^7$ is hydrogen, $C_{1-6}$alkyl optionally substituted with aryl, $(R^4)(R^5)N$—, pyrrolidinyl, piperidinyl, piperazinyl, 4-($C_{1-4}$alkyl)-piperazinyl or with morpholinyl;

(6-b) $R^7$ is hydrogen, $C_{1-6}$alkyl optionally substituted with $(R^4)(R^5)N$—, pyrrolidinyl or with piperidinyl;

(6-c) $R^7$ is hydrogen, $C_{1-6}$alkyl optionally substituted with pyrrolidinyl or with piperidinyl.

Further embodiments of the present invention are those compounds of formula (I) or any of the subgroups of compounds of formula (I) wherein (7) each aryl independently is phenyl optionally substituted with 1, 2 or 3 substituents each independently selected from $C_{1-6}$alkyl, $C_{1-4}$alkoxy, cyano and nitro.

Further embodiments of the present invention are those compounds of formula (I) or any of the subgroups of compounds of formula (I) wherein (8) Het is a 5-membered ring system wherein one, two, three or four ring members are heteroatoms each independently selected from the group consisting of nitrogen, oxygen and sulfur, and wherein the remaining ring members are carbon atoms; and, where possible, any nitrogen ring member may optionally be substituted with $C_{1-4}$alkyl; any ring carbon atom may, each individually and independently, optionally be substituted with a substituent selected from the group consisting of $C_{1-4}$alkyl, $C_{3-7}$cycloalkyl, halo, cyano, trifluoromethyl, cyano$C_{1-4}$alkyl, mono- or di($C_{1-4}$alkyl)amino, mono- or di($C_{1-4}$alkyl)amino$C_{3-6}$alkenyl, isoxazolyl, aryl, hydroxycarbonyl, $C_{1-4}$alkyloxy-carbonyl, oxo, or thio; and wherein the foregoing isoxazolyl may optionally be substituted with $C_{1-4}$alkyl;

(8-a) Het is furanyl, thienyl, pyrrolyl, oxazolyl, thiazolyl, imidazolyl, isoxazolyl, isothiazolyl, pyrazolyl, oxadiazolyl, thiadiazolyl, triazolyl, or tetrazolyl, each optionally substituted with a substituent selected from $C_{1-4}$alkyl, $C_{2-6}$alkenyl, $C_{3-7}$cycloalkyl, hydroxy, mercapto, $C_{1-4}$alkoxy, halo, amino, cyano, trifluoromethyl, hydroxy$C_{1-4}$alkyl, cyano$C_{1-4}$alkyl, mono- or di($C_{1-4}$alkyl)amino, amino-$C_{1-4}$alkyl, mono- or di($C_{1-4}$alkyl)amino$C_{1-4}$alkyl, aryl$C_{1-4}$alkyl, amino$C_{3-6}$alkenyl, mono- or di($C_{1-4}$alkyl)amino$C_{3-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, $C_{1-4}$alkyloxycarbonyl, mono- or di($C_{1-4}$alkyl)aminocarbonyl, $C_{1-4}$alkylcarbonyl; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with $C_{1-4}$alkyl;

(8-b) Het is furanyl, thienyl, pyrrolyl, oxazolyl, thiazolyl, imidazolyl, isoxazolyl, isothiazolyl, pyrazolyl, oxadiazolyl, thiadiazolyl, triazolyl, or tetrazolyl, each optionally substituted with a substituent selected from $C_{1-4}$alkyl, $C_{2-6}$alkenyl, $C_{3-7}$cycloalkyl, hydroxy, mercapto, $C_{1-4}$alkoxy, halo, amino, cyano, trifluoromethyl, hydroxy$C_{1-4}$alkyl, cyano$C_{1-4}$alkyl, mono- or di($C_{1-4}$alkyl) amino, amino$C_{1-4}$alkyl, aryl$C_{1-4}$alkyl, amino$C_{3-6}$alkenyl, mono- or di($C_{1-4}$alkyl)amino-$C_{3-6}$alkenyl, furanyl, thienyl, aryl, hydroxycarbonyl, aminocarbonyl, C14alkyloxycarbonyl, mono- or di($C_{1-4}$alkyl)aminocarbonyl, $C_{1-4}$alkylcarbonyl;

(8-c) Het is furanyl, thienyl, thiazolyl, isoxazolyl, oxadiazolyl, thiadiazolyl, triazolyl, or tetrazolyl, each optionally substituted with a substituent selected from $C_{1-4}$alkyl, $C_{2-6}$alkenyl, $C_{3-7}$cycloalkyl, hydroxy, mercapto, $C_{1-4}$alkoxy, halo, amino, cyano, trifluoromethyl, cyano$C_{1-4}$ alkyl, aryl$C_{1-4}$alkyl, amino$C_{3-6}$alkenyl, mono- or di($C_{1-4}$alkyl)amino$C_{3-6}$alkenyl, furanyl, thienyl, aryl, hydroxycarbonyl, $C_{1-4}$alkyloxycarbonyl, $C_{1-4}$alkylcarbonyl;

(8-d) Het is furanyl, thienyl, thiazolyl, isoxazolyl, oxadiazolyl, thiadiazolyl, triazolyl, or tetrazolyl, each optionally substituted with a substituent selected from $C_{1-4}$alkyl, $C_{3-7}$cycloalkyl, hydroxy, mercapto, $C_{1-4}$alkoxy, halo, trifluoromethyl, cyano$C_{1-4}$alkyl, aryl$C_{1-4}$alkyl, furanyl, thienyl, aryl, hydroxycarbonyl, $C_{1-4}$alkyloxycarbonyl, $C_{1-4}$alkylcarbonyl.

An interesting subgroup of compounds of formula (I) comprises those compounds, which may be represented by formula:

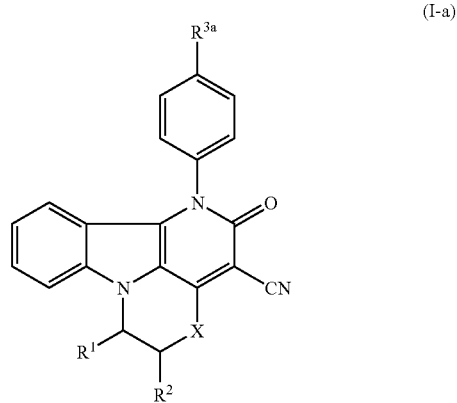

(I-a)

wherein $R^1$, $R^2$, $R^{3a}$ and X are as specified in the defintions of the compounds of formula (I) or any of the subgroups thereof.

A particular subgroup of compounds of the invention are those compounds of formula (I) or any of the subgroups specified herein, wherein the compound of formula (I) is present as an acid-addition salt form, wherein the salt preferably is selected from trifluoroacetate, fumarate, methanesulfonate, oxalate, acetate and citrate.

Compounds of interest are compounds number 1, 4, 5, 7 and 8, in particular compound 1, as listed in table 1 following the experimental part, and the salts and possible stereoisomers thereof.

The compounds of the present invention show antiretroviral properties, in particular they are active against HIV. In particular, the compounds of formula (I) are inhibitors of the HIV reverse transcriptase. In general, the compounds of the present invention have a good selectivity as measured by the ratio between $EC_{50}$ and $CC_{50}$ and show good activity against resistant mutant strains and even against multi-drug resistant strains. Currently used HIV reverse transcriptase ("RT") inhibitors lose effectivity due to mutations, which cause changes in the RT enzyme, resulting in a less effective interaction of the inhibitor with the RT enzyme, whereby the virus becomes less "sensitive" to the RT inhibitor. Mutants where the RT inhibitor no longer is effective are referred to as "resistant mutants". "Multi-drug resistance" is where the mutants are resistant to multiple other HIV RT inhibitors. The resistance of a mutant to a particular HIV RT inhibitor is expressed by the ratio of the $EC_{50}$ of the HIV RT inhibitor measured with mutant HIV RT to the $EC_{50}$ of the same HIV RT inhibitor measured with wild type HIV RT. This ratio is also referred to as "fold change" in resistance (FR). An $EC_{50}$ value represents the amount of the compound required to protect 50% of the cells from the cytopathogenic effect of the virus.

Many of the mutants occurring in the clinic have a fold resistance of 100 or more against the commercially available HIV NNRTIs, like nevirapine, efavirenz, delavirdine. Clinically relevant mutants of the HIV reverse transcriptase enzyme may be characterized by a mutation at codon position 100, 103 and 181. As used herein a codon position means a position of an amino acid in a protein sequence. Mutations at positions 100, 103 and 181 relate to non-nucleoside RT inhibitors.

Of interest are those compounds of formula (I) having a fold resistance ranging between 0.01 and 100, in particular between 0.1 and 30, more in particular between 0.1 and 20, or further in particular between 0.1 and 10, against at least one mutant HIV reverse transcriptase. Of interest are those compounds of formula (I) having a fold resistance in the range of 0.01 to 100, in particular between 0.1 and 30, more in particular between 0.1 and 20, or further in particular between 0.1 and 10, against HIV species having at least one or at least two mutation(s) in the amino acid sequence of HIV reverse transcriptase as compared to the wild type sequence at a position selected from 100, 103 and 181.

In general, are active against mutant strains that show restistance toward currently available NNRTIs such as nevirapine, efavirenz, delavirdin. The compounds of the invention interact through a unique mechanism of action in that they are competitive NNRT inhibitors and moreover show increased activity when co-administered with a nucleoside phosphate such as ATP. Therefore the compounds of the invention may find use in HIV drug combinations with currently available NNRTIs.

The compounds of the invention may be used to treat other diseases associated with HIV infection, which include thrombocytopaenia, Kaposi's sarcoma and infection of the central nervous system characterized by progressive demyelination, resulting in dementia and symptoms such as, progressive dysarthria, ataxia and disorientation. Still other diseases that have been associated with and that may be treated using the compounds of this invention comprise peripheral neuropathy, progressive generalized lymphadenopathy (PGL) and AIDS-related complex (ARC).

Due to their favourable pharmacological properties, particularly their activity against HIV, the compounds of the present invention may be used as medicines against above-mentioned diseases or in the prophylaxis thereof. Said use as a medicine or method of treatment comprises the systemic administration to HIV-infected subjects of an amount effective to combat the conditions associated with HIV.

In a further aspect, the present invention concerns the compound of formula (I) or any subgroup thereof for use as a medicament. In another aspect, the present invention concerns the use of a compound of formula (I) or any subgroup thereof, for the manufacture of a medicament for preventing, treating or combating HIV infection or a disease associated with HIV infection.

In another aspect, the present invention concerns the use of a compound of formula (I) or any subgroup thereof, for the manufacture of a medicament useful for inhibiting replication of HIV, in particular HIV having a mutant HIV reverse transcriptase, more in particular a multi-drug resistant mutant HIV reverse transcriptase.

In yet another aspect, the present invention relates to the use of a compound of formula (I) or any subgroup thereof in the manufacture of a medicament useful for preventing, treating or combating a disease associated with HIV viral infection wherein the reverse transcriptase of the HIV virus is mutant, in particular a multi-drug resistant mutant HIV reverse transcriptase.

The compounds of formula (I) or any subgroup thereof are also useful in a method for preventing, treating or combating HIV infection or a disease associated with HIV infection in a mammal, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a mutant HIV virus, comprising administering to said mammal an effective amount of a compound of formula (I) or any subgroup thereof.

In another aspect, the compounds of formula (I) or any subgroup thereof are useful in a method for preventing, treating or combating infection or disease associated with infection of a mammal with a multi drug-resistant HIV virus, comprising administering to said mammal an effective amount of a compound of formula (I) or any subgroup thereof.

In yet another aspect, the compounds of formula (I) or any subgroup thereof are useful in a method for inhibiting replication of a HIV virus, in particular a HIV virus having a mutant HIV reverse transcriptase, more in particular a multi-drug resistant mutant HIV reverse transcriptase, comprising administering to a mammal in need thereof an effective amount of a compound of formula (I) or any subgroup thereof.

Preferably, a mammal as mentioned in the methods of this invention is a human being.

The compounds of the present invention may also find use in inhibiting HIV in ex vivo samples containing HIV or expected to be exposed to HIV. Hence, the present compounds may be used to inhibit HIV present in a body fluid sample that contains or is suspected to contain or be exposed to HIV.

A number of synthesis procedures to prepare compounds of the present invention are described below. In the preparations described below, the reaction products may be isolated and, if necessary, further purified according to methodologies generally known in the art such as, for example, extraction, crystallization, trituration and chromatography.

The compounds of formula (I) can be prepared as outlined in the following scheme. In this scheme, $R^1$, $R^2$, $R^3$ and X are as defined above.

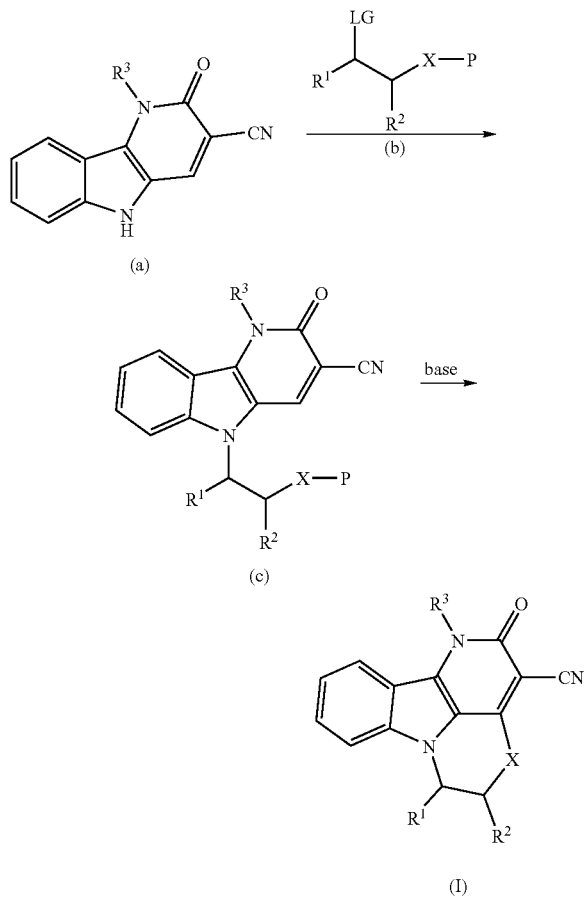

The starting material (a) may be produced following the synthesis schemes presented in patent application number WO04/046143. Starting materials wherein $R^3$ is a monocyclic or bicyclic aromatic heterocyclic ring system can be made by analogous methods.

The starting material (a) is reacted with intermediate (b) in an alkylation reaction to yield an intermediate (c), which subsequently is cyclized to yield end products (I). In intermediate (b), LG is a leaving group or a leaving group precursor which in situ may be converted into a suitable leaving group such as e.g. an alcohol function which is reacted with $PCl_3$, $POCl_3$ or by a Mitsunobu-type reaction using an azodicarboxylate/triphenyl phosphine reagent to produce a leaving group from the alkylalcohol and subsequent reaction with the appropriate amine P in the radical —X—P is hydrogen or a suitable protecting group, and X, $R^1$ and $R^2$ have the meaning as indicated above. Suitable protecting groups comprise benzyl, benzyloxycarbonyl, t-butyloxycarbonyl. The group P is removed prior to cyclization of intermediate (c). Intermediate (c) can be cyclized by addition of a base.

Alternatively, when an alky, hydroxyalkyl, or aminoalkyl is to be introduced as substituent $R^1$, a starting material (a) is reacted with a glycerine derivative with two primary alcohols protected, such as with an acetal group. Said glycerine derivative is coupled with the nitrogen atom of the indol of the starting material (a). By subsequent addition of an acid, the acid-labile protecting group previously introduced, i.e. the acetal function, is deprotected to result in a diol (e). Following the addition of a base, cyclisation results to compounds (I-a) and by addition of a suitable reagent to introduce leaving groups, such as mesyl chloride or tosyl chloride, the alcohol is transformed into a leaving group. A subsequent substitution reaction with ammonia or a mono-, di-substituted amino, results in compounds of formula (I-b), which are compounds of formula (I) wherein $R^1$ is aminomethyl and $R^2$ is hydrogen. These reactions are represented in the following reaction scheme in which $R^3$, $R^4$ and $R^5$ are as defined above.

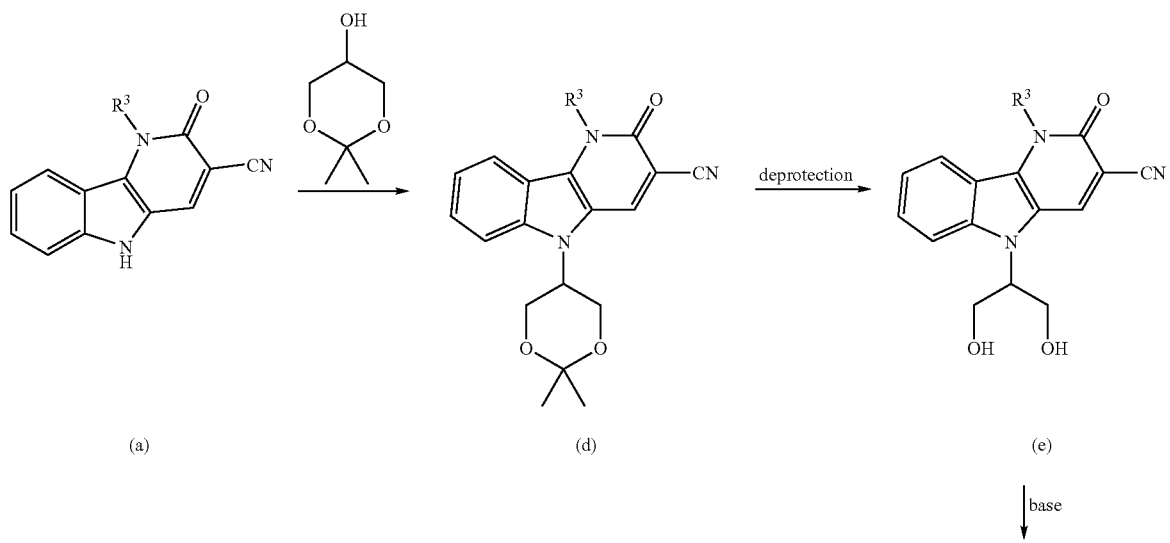

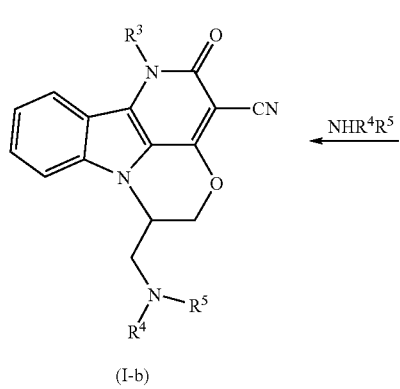 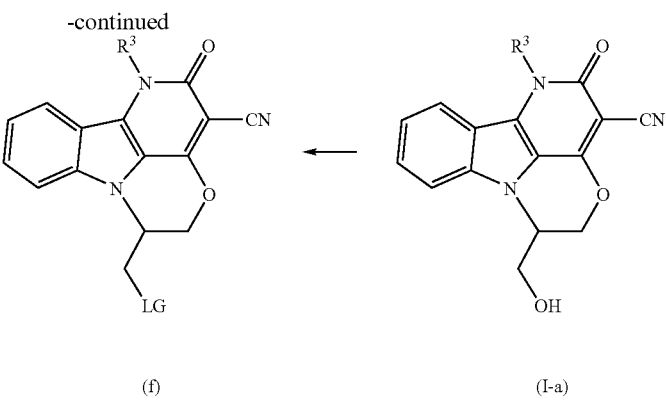

(I-b)    (f)    (I-a)

The compounds of formula (I) may be transferred into other compounds of formula (I) with different substitution using art-known transformation techniques. For instance, the compounds of formula (I) having an aromatic substituent, which is nitro may be reduced to the corresponding amino analogs, which in turn may be further derivatized.

Compounds of formula (I) wherein $R^3$ is substituted with halo can be converted to the corresponding cyano compounds by reacting the starting materials with a suitable cyano nucleophile, e.g. copper(I) cyanide.

The compounds of formula (I) may also be converted to the corresponding N-oxide forms following art-known procedures for converting a tri-substituted nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The compounds of this invention can thus be used as such but preferably are used in the form of pharmaceutical compositions. Thus in a further aspect, the present invention relates to pharmaceutical compositions that as active ingredient contain an effective dose of a compounds of formula (I) in addition to a carrier which may comprise customary pharmaceutically innocuous excipients and auxiliaries. The pharmaceutical compositions normally contain 0.1 to 90% by weight of a compound of formula (I). The pharmaceutical compositions can be prepared in a manner known per se to one of skill in the art. To this purpose, a compound of formula (I), together with one or more solid or liquid carrier which may comprise pharmaceutical excipients and/or auxiliaries and, if desired, in combination with other pharmaceutical active compounds, are brought into a suitable administration form or dosage form.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries that are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MIV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo-[4,5,1-jk] [1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfmavir (AG-1343), atazanavir (BMS 232, 632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCR5 antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); a maturation inhibitor for example is PA-457 (Panacos Pharmaceuticals); inhibitors of the viral integrase; ribonucleotide reductase inhibitors (cellular inhibitors), e.g. hydroxyurea and the like.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines or modulators of chemokines, chemokine receptors (e.g. CCR5, CXCR4), modulators chemokine receptors, or hormones (e.g. growth hormone) to ameliorate, combat, or eliminate HIV infection and its symptoms. Such combination therapy in different formulations, may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations, may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefore such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, ethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavours.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions, which are less homogeneous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide, which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those that physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds of the present invention may be incorporated in hydrophilic polymers and this mixture may be applied as a coat film on small beads. In one embodiment, these beads comprise a central, rounded or spherical core, a coating film of a hydrophilic polymer and an antiretroviral agent and a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof. The thus obtained coated beads have a good bioavailability and are suitable for preparing oral dosage forms.

The route of administration may depend on the condition of the subject, co-medication and the like.

Another aspect of the present invention concerns a kit or container comprising a compound of formula (I) in an amount effective for use as a standard or reagent in a test or assay for determining the ability of a potential pharmaceutical to inhibit HIV reverse transcriptase, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram®. The Antivirogram® is a highly automated, high throughput, second generation, recombinant assay that can measure susceptibility, especially viral susceptibility, to the compounds of the present invention. (Hertogs K., et al. *Antimicrob Agents Chemother*, 1998; 42(2):269-276, incorporated by reference).

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components such as albumine. The compounds of the present invention may be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight co-medication and individual responsiveness of the human or animal to be treated and on whether the therapy is acute or prophylactic. Customarily, the daily dose of a compound of formula (I) in the case of administration to a patient approximately 75 kg in weight is 1 mg to 3 g, preferably 3 mg to 1 g, more preferably, 5 mg to 0.5 g. The dose can be administered in the form of an individual dose, or divided into several, e.g. two, three, or four, individual doses.

EXAMPLES

The following examples illustrate compounds of formula (I), the preparation and pharmacological properties thereof, and should not be construed as a limitation of the scope of the present invention.

Example 1

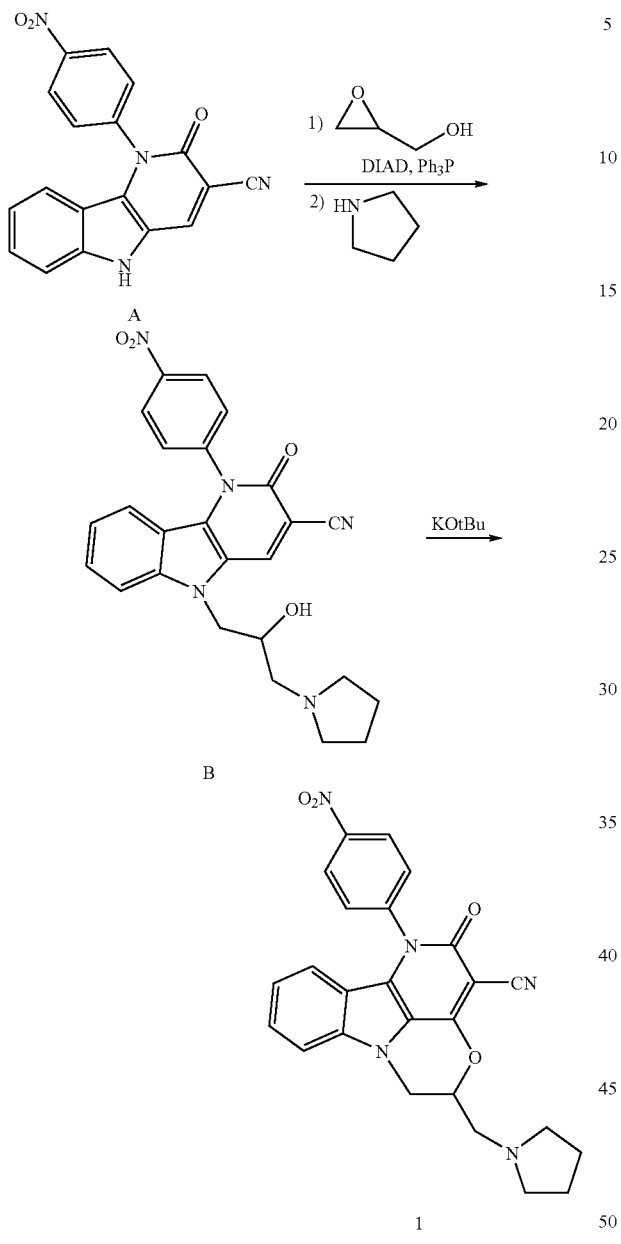

A mixture of intermediate A (2.558 mmol, 845 mg), glycidol (2 equiv., 5.117 mmol, 379 mg) and diisopropyl azodicarboxylate (2 equiv., 5.117 mmol, 1035 mg) were stirred in DMF (10 ml). The reaction mixture was cooled on ice and triphenylphosphine (2 equiv., 5.117 mmol, 1342 mg) was added. The reaction mixture was stirred at room temperature overnight. Pyrrolidine (20 equiv., 51.166 mmol, 3639 mg) was added and the reaction mixture was stirred at 50° C. for 4 h. Water (25 ml) was added causing precipitation of the reaction product. The precipitate was isolated by filtration, and washed successively with water, ethanol and diisopropyl ether affording intermediate B (1060 mg, yield=91%, purity (LC)>95%).

A mixture of intermediate B (0.1639 mmol, 75 mg) in DMF (3 ml) was stirred on ice for 15 min. Then, potassium tert-butoxide (1.5 equiv., 0.2459 mmol, 27.6 mg) was added and the reaction mixture was stirred overnight at room temperature. Water (5 ml) was added, the reaction mixture was extracted with dichloromethane and the organic phase was washed with brine. After drying ($MgSO_4$), the organic phase was concentrated, affording compound 1 (73 mg, yield=94%, purity (LC)>95%); $^1$H NMR (δ, DMSO-D6): 8.72 (1H, br s), 8.47 (2H, d, J=8.7 Hz), 7.79 (2H, d, J=8.7 Hz), 7.66 (1H, d, J=8.4 Hz), 7.37 (1H, t, J=7.7 Hz), 6.92 (1H, t, J=7.7 Hz), 6.31 (1H, d, J=8.3 Hz), 4.33 (2H, t, J≈5 Hz), 3.86 (2H, t, J≈5 Hz).

Example 2

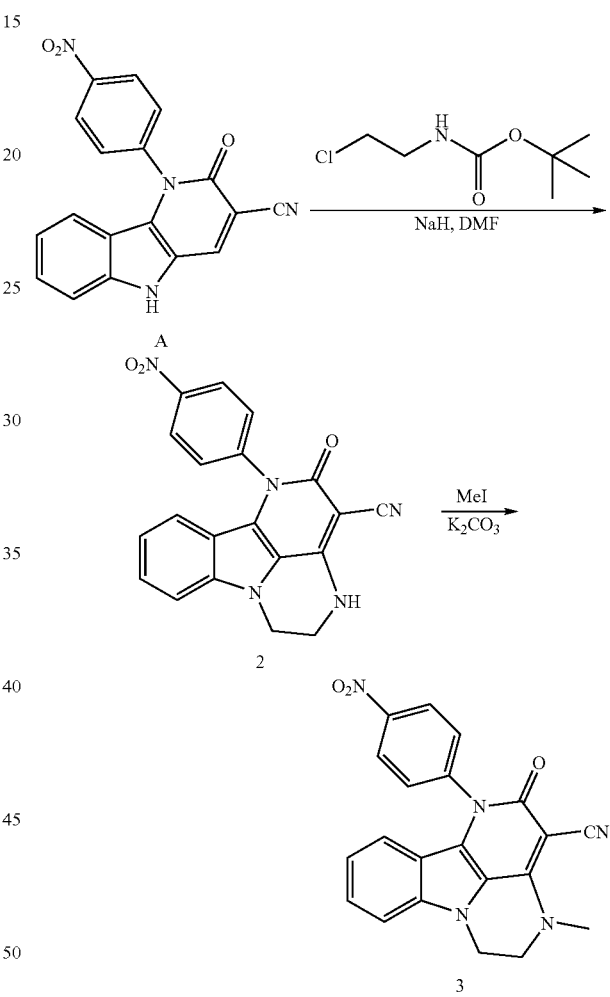

Sodium hydride (3.00 equiv., 23.62 mmol, 945 mg, 60%) was added to a stirred solution of intermediate A (7.87 mmol, 2600 mg) in DMF (50 ml) and the mixture was heated for 1 at 60° C. After cooling to room temperature, N-tBoc-2-chloroethylamine (2.00 equiv., 15.74 mmol, 2828 mg) was added and the mixture was heated at 60 ° C. for 3 h. The reaction product was precipitated by the addition of water and isolated by filtration. The precipitate was washed with isopropanol and diisopropyl ether, affording compound 2 (1213 mg, yield=41%, purity (LC)=93%); $^1$H NMR (δ, DMSO-D6): 8.48 (2H, d, J=8.8 Hz), 7.78 (2H, d, J=8.8 Hz), 7.63 (1H, d, J=8.5 Hz), 7.36 (1H, t, J≈8 Hz), 6.90 (1H, t, J≈8 Hz), 6.26 (1H, d, J=8.2 Hz), 4.38 (2H, t, J≈5 Hz), 3.97 (2H, t, J≈5 Hz), 3.62 (3H, s).

Methyl iodide (1.50 equiv., 0.404 mmol, 57 mg) and potassium carbonate (2.00 equiv., 0.538 mmol, 74 mg) were added to a solution of compound 2 (0.269 mmol, 100 mg) in DMF (10 ml). The reaction mixture was heated under reflux for 2.5 h. The reaction mixture was cooled to room temperature, precipitated with water and filtered. The precipitate was washed with isopropanol and diisopropyl ether, affording compound 3 (44 mg, yield=42%, purity=98%).

Example 3

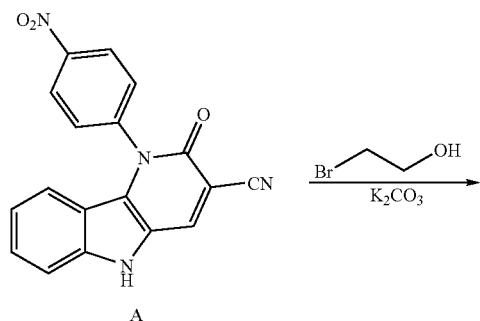

A

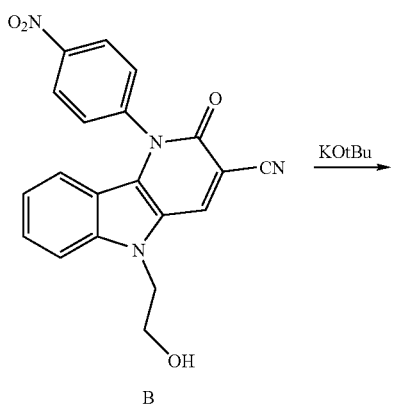

B

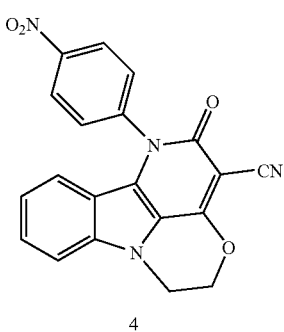

4

A mixture of intermediate A (0.606 mmol, 200 mg), potassium carbonate (2 equiv., 1.21 mmol, 167 mg), bromoethanol (2 equiv., 1.21 mmol, 151 mg) and tetrabutyl-ammonium iodide (2 equiv., 1.21 mmol, 447 mg) in dry DMF (4 ml) was heated at 70° C. under $N_2$ atmosphere for 48 h. After cooling to room temperature, the reaction mixture was concentrated and the residue partitioned between ethyl acetate (200 ml) and water (100 ml). The organic layer was dried ($Na_2SO_4$) and concentrated. The crude material was purified by column chromatography on silica gel (eluens: $CH_2Cl_2$/AcOEt/petroleum ether, 7:1:2), affording intermediate B as a yellow powder. (120 mg, yield=53%, purity (LC)>95%).

Potassium tert-butoxide (1.2 equiv., 0.160 mmol, 18 mg) was added at room temperature under $N_2$ atmosphere to a solution of intermediate B (0.134 mmol, 50 mg) in dry DMF (2 ml). After 30 min at room temperature, the reaction mixture was acidified to pH 5 with acetic acid and partitioned between water (30 ml) and ethyl acetate (150 ml). The organic layer was dried ($Na_2SO_4$) and concentrated. Purification by column chromatography on silica gel (eluens: $CH_2Cl_2$/AcOEt/MeOH, 5:4:1) afforded compound 4 as a yellow powder (5.1 mg, yield=10%, purity (LC)>95%).

Example 4

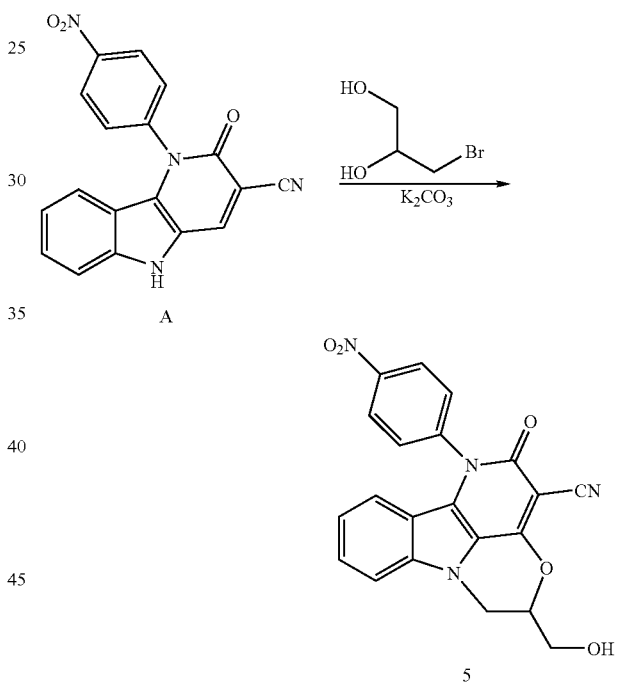

A mixture of intermediate A (1.51 mmol, 500 mg), potassium carbonate (2 equiv., 3.03 mmol, 418 mg), 3-bromopropane-1,2-diol (2 equiv., 3.03 mmol, 469 mg) and tetrabutylammonium iodide (1 equiv., 1.51 mmol, 580 mg) in dry DMF (10 ml) was heated at 90° C. under $N_2$ atmosphere for 2 h. After cooling to room temperature, the reaction mixture was concentrated and the residue partitioned between ethyl acetate (200 ml) and water (100 ml). The organic layer was dried ($Na_2SO_4$) and concentrated. The crude material was purified by column chromatography on silica gel (eluent: $CH_2Cl_2$/THF, 2:1), affording compound 5 as a yellow powder (6.5 mg, yield =1.1%, purity (LC)>95%).

The following table lists examples of compounds of the present invention which compounds are prepared analogous those of the foregoing synthesis schemes.

TABLE 1

[Structure: tetracyclic indole-fused pyridinone core with substituents R³ᵃ on para-phenyl on N, CN at pyridinone, and a ring containing X with R¹ and R² substituents]

| Comp. No. | Synthesis Example | R¹ | R² | R³ᵃ | X |
|---|---|---|---|---|---|
| 1 | 1 | —H | —CH₂—N(pyrrolidinyl) | —NO₂ | —O— |
| 2 | 2 | —H | —H | —NO₂ | —NH— |
| 3 | 2 | —H | —H | —NO₂ | —N(CH₃)— |
| 4 | 3 | —H | —H | —NO₂ | —O— |
| 5 | 4 | —H | —CH₂—OH | —NO₂ | —O— |
| 6 | 2 | —H | —H | —NO₂ | —N(CH₂CH₂-pyrrolidinyl)— |
| 7 | 1 | —H | —CH₂—N(piperidinyl) | —NO₂ | —O— |
| 8 | 1 | —H | —CH₂—N(Et)₂ | —NO₂ | —O— |
| 9 | 1 | —H | —CH₂—N(morpholinyl) | —NO₂ | —O— |
| 10 | 1 | —H | —CH₂—N(iPr)₂ | —NO₂ | —O— |
| 11 | 1 | —H | —CH₂—N(CH₃)₂ | —NO₂ | —O— |

In the above table, the symbol ⌇ indicates the bond through which the radical is connected to the remainder of the molecule.

The following are a number of compounds of the invention, identified by the compound number as listed in the above table 1, with corresponding NMR data:

Compound 7

$^1$H NMR (δ, DMSO-D6): 8.52 (2H, d, J=9.0 Hz), 7.88-7.84 (2H, m), 7.74 (1H, d, J=8.2 Hz), 7.46 (1H, t, J≈8 Hz), 6.97 (1H, t, J≈8 Hz), 6.37 (1H, d, J=8.2 Hz), 5.22-5.15 (1H, m), 4.74-4.69 (1H, m), 4.31-4.26 (1H, m), 2.98-2.95 (2H, m), 2.67-2.61 (4H, m), 1.04-1.00 (6H, m).

Compound 9

$^1$H NMR (δ, DMSO-D6): 8.52 (2H, d, J=8.6 Hz), 7.89-7.83 (2H, m), 7.74 (1H, d, J=8.5 Hz), 7.45 (1H, t, J≈8 Hz), 6.97 (1H, t, J≈8 Hz), 6.37 (1H, d, J=8.3 Hz), 5.14-5.08 (1H, m), 4.67-4.62 (1H, m), 4.37-4.32 (1H, m), 3.11-2.89 (4H, m), 1.03-1.01 (12H, m).

Compound 10

$^1$H NMR (δ, DMSO-D6): 8.53 (2H, d, J=8.8 Hz), 7.88-7.84 (2H, m), 7.74 (1H, d, J=8.5 Hz), 7.46 (1H, t, J≈8 Hz), 6.97 (1H, t, J≈8 Hz), 6.37 (1H, d, J=8.2 Hz), 5.29-5.22 (1H, m), 4.80-4.75 (1H, m), 4.25-4.17 (1H, m), 2.88-2.82 (2H, m), 2.33 (6H, s).

Antiviral Analyses

The compounds of the present invention were examined for anti-viral activity in a cellular assay, which was performed according to the following procedure.

HIV- or mock-infected MT4 cells were incubated for five days in the presence of various concentrations of the inhibitor. At the end of the incubation period, the replicating virus in the control cultures has killed all HIV-infected cells in the absence of any inhibitor. Cell viability was determined by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution was monitored at 540 nm. The values correlate directly to the number of living cells remaining in the culture at the completion of the five day incubation. The inhibitory activity of the compound was monitored on the virus-infected cells and was expressed as $EC_{50}$. These values represent the amount of the compound required to protect 50% of the cells from the cytopathogenic effect of the virus. The toxicity of the compound can be measured on the mock-infected cells and is expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor.

The following Table 2 lists $EC_{50}$ values against wild-type HIV-LAI strain for a number of compounds of the invention.

TABLE 2

| Comp. No. | $EC_{50}$ (μM) |
|---|---|
| 1 | 0.34 |
| 2 | 3.05 |
| 3 | 1.88 |
| 4 | 0.51 |
| 5 | 0.74 |
| 6 | 9.30 |
| 7 | 0.27 |
| 8 | 0.37 |
| 9 | 4.51 |

TABLE 2-continued

| Comp. No. | $EC_{50}$ (μM) |
|---|---|
| 10 | 1.96 |
| 11 | 0.16 |

Formulations

Capsules

Compound 1 is dissolved in a mixture of ethanol and methylene chloride and hydroxypropylmethylcellulose (HPMC) 5 mPa·s is dissolved in ethanol. Both solutions are mixed such that the w/w ratio compound/polymer is 1/3 and the mixture is spray dried in standard spray-drying equipment. The spray-dried powder, a solid dispersion, is subsequently filled in capsules for administration. The drug load in one capsule is selcted such that it ranges between 50 and 100 mg, depending on the capsule size used. Following the same procedures, capsule formulations of the other compounds of formula (I) can be prepared.

Film-Coated Tablets

Preparation of Tablet Core

A mixture of 1000 g of compound 1, 2280 g lactose and 1000 g starch is mixed well and thereafter humidified with a solution of 25 g sodium dodecyl sulfate and 50 g polyvinylpyrrolidone in about 1000 ml of water. The wet powder mixture is sieved, dried and sieved again. Then there is added 1000 g microcrystalline cellulose and 75 g hydrogenated vegetable oil. The whole is mixed well and compressed into tablets, giving 10,000 tablets, each comprising 100 mg of the active ingredient.

Coating

To a solution of 10 g methylcellulose in 75 ml of denaturated ethanol there is added a solution of 5 g of ethylcellulose in 150 ml of dichloromethane. Then there is added 75 mi of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

Following the same procedures, tablet formulations of the other compounds of formula (I) can be prepared.

The invention claimed is:

1. A compound of formula:

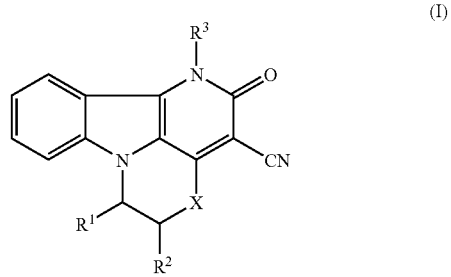

(I)

the salts and stereoisomeric forms thereof, wherein $R^1$ and $R^2$ are each, independently, hydrogen or $C_{1-10}$alkyl, which may be optionally substituted with a substituent selected from hydroxy, cyano, NR⁴R⁵, pyrrolidinyl, piperidinyl, homopiperidinyl, piperazinyl, 4-(C$_{1-4}$alkyl)-piperazinyl, morpholinyl, thiomorpholinyl, 1-oxothiomorpholinyl, 1,1-dioxo-thiomorpholinyl, aryl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, pyridyl, pyrimidinyl, pyrazinyl, pyridazinyl, triazinyl, hydroxycarbonyl, C$_{1-4}$alkylcarbonyl, (R⁴)(R⁵)N-carbonyl, C$_{1-4}$alkyloxycarbonyl, pyrrolidin-1-ylcarbonyl, piperidin-1-ylcarbonyl, homopiperidin-1-ylcarbonyl, piperazin-1-ylcarbonyl, 4-(C$_{1-4}$alkyl)-piperazin-1-ylcarbonyl, morpholin-1-yl-carbonyl, thiomorpholin-1-ylcarbonyl, 1-oxothiomorpholin-1-ylcarbonyl and 1,1-dioxo-thiomorpholin-1-ylcarbonyl;

R³ is a radical of formula

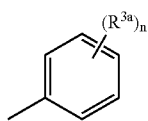

(a)

wherein n is 1, 2 or 3;

R$^{3a}$ is nitro, cyano, amino, halo, hydroxy, C$_{1-4}$alkyloxy, hydroxycarbonyl, aminocarbonyl, C$_{1-4}$alkyloxycarbonyl, mono- or di(C$_{1-4}$alkyl)aminocarbonyl, C$_{1-4}$alkylcarbonyl, methanimidamidyl, mono- or di(C$_{1-4}$alkyl)methanimidamidyl, N-hydroxy-methanimidamidyl or Het; or R³ is a monocyclic or bicyclic aromatic heterocyclic ring system, wherein one, two, three or four ring members are heteroatoms each independently selected from nitrogen, oxygen and sulfur, and wherein the remaining ring members are carbon atoms; and wherein each of said heterocyclic ring systems may optionally be substituted with one, two, three, four or five substituents each independently selected from halo, cyano, nitro, C$_{1-6}$alkyl, hydroxyC$_{1-6}$alkyl, C$_{1-4}$alkoxyC$_{1-6}$alkyl, (R$^{5a}$)(R$^{5b}$)N—C$_{1-4}$alkyl, polyhaloC$_{1-6}$alkyl, C$_{3-7}$cycloalkyl, arylC$_{1-6}$alkyl, formyl, C$_{1-6}$alkylcarbonyl, a radical —COOR⁶, (R$^{5a}$)(R$^{5b}$)N-carbonyl, (R$^{5a}$)(R$^{5b}$)N-sulfonyl, hydroxy, C$_{1-6}$alkyloxy, arylC$_{1-6}$alkyloxy, polyhalo-C$_{1-6}$alkyloxy, formyloxy, C$_{1-6}$alkylcarbonyloxy, aryloxy, a radical (R$^{5a}$)(R$^{5b}$)N—, formylamino, C$_{1-6}$alkylcarbonylamino, C$_{1-6}$alkyloxycarbonylamino, C$_{1-6}$alkylsulfonylamino, mercapto, C$_{1-6}$alkylthio, arylthio, arylC$_{1-6}$alkylthio, C$_{1-6}$alkylsulfinyl, C$_{1-6}$alkylsulfonyl, aryl, —CH(=N—O—R$^{5a}$), and —C(=NH)—NH—R$^{5a}$;

X is —NR⁷—, —O— or —S—;

R⁴ and R⁵ each independently are hydrogen, C$_{1-6}$alkyl or C$_{1-6}$alkyl substituted with a substituent selected from amino, mono- or di-(C$_{1-4}$alkyl)amino, pyrrolidinyl, piperidinyl, homopiperidinyl, piperazinyl, 4-(C$_{1-4}$alkyl)-piperazinyl, morpholinyl, thiomorpholinyl, 1-oxothiomorpholinyl and 1,1-dioxo-thiomorpholinyl;

each R$^{5a}$, R$^{5b}$ independently is hydrogen, C$_{1-4}$alkyl or arylC$_{1-4}$alkyl;

R⁶ is hydrogen, C$_{1-4}$alkyl or arylC$_{1-4}$alkyl;

R⁷ is hydrogen, C$_{1-6}$alkyl, optionally substituted with aryl, (R⁴)(R⁵)N—, pyrrolidinyl, piperidinyl, homopiperidinyl, piperazinyl, 4-(C$_{1-4}$alkyl)-piperazinyl, morpholinyl, thiomorpholinyl, 1-oxothiomorpholinyl or with 1,1-dioxo-thiomorpholinyl;

each aryl independently is phenyl optionally substituted with 1, 2 or 3 substituents each independently selected from C$_{1-6}$alkyl, C$_{1-4}$alkoxy, halo, hydroxy, amino, trifluoromethyl, cyano, nitro, hydroxyC$_{1-6}$alkyl, cyanoC$_{1-6}$alkyl, mono- or di(C$_{1-4}$alkyl)amino, aminoC$_{1-4}$alkyl, mono- or di(C$_{1-4}$alkyl)aminoC$_{1-4}$alkyl;

Het is a 5- or 6-membered ring system wherein one, two, three or four ring members are heteroatoms each individually and independently selected from nitrogen, oxygen and sulfur, and wherein the remaining ring members are carbon atoms; and, where possible, any nitrogen ring member may optionally be substituted with C$_{1-4}$alkyl; any ring carbon atom may, each individually and independently, optionally be substituted with a substituent selected from C$_{1-4}$alkyl, C$_{2-6}$alkenyl, C$_{3-7}$cycloalkyl, hydroxy, C$_{1-4}$alkoxy, halo, amino, cyano, trifluoromethyl, hydroxyC$_{1-4}$alkyl, cyanoC$_{1-4}$alkyl, mono- or di(C$_{1-4}$alkyl)amino, aminoC$_{1-4}$alkyl, mono- or di(C$_{1-4}$ alkyl)aminoC$_{1-4}$alkyl, arylC$_{1-4}$alkyl, aminoC$_{3-6}$alkenyl, mono- or di(C$_{1-4}$alkyl)aminoC$_{3-6}$alkenyl, furanyl, thienyl, pyrrolyl, oxazolyl, thiazolyl, imidazolyl, isoxazolyl, isothiazolyl, pyrazolyl, oxadiazolyl, thiadiazolyl, triazolyl, tetrazolyl, aryl, hydroxycarbonyl, aminocarbonyl, C$_{1-4}$alkyloxycarbonyl, mono- or di(C$_{1-4}$ alkyl)aminocarbonyl, C$_{1-4}$alkylcarbonyl, oxo, and thio; and wherein any of the foregoing furanyl, thienyl, pyrrolyl, oxazolyl, thiazolyl, imidazolyl, isoxazolyl, isothiazolyl, pyrazolyl, oxadiazolyl, thiadiazolyl and triazolyl moieties may optionally be substituted with C$_{1-4}$alkyl.

2. A compound according to claim 1 wherein R¹ is hydrogen.

3. A compound according to claim 1, wherein R² is hydrogen, C$_{1-6}$alkyl optionally substituted with hydroxy, di-C$_{1-4}$alkylamino, pyrrolidinyl, piperidinyl or with morpholinyl.

4. A compound according to claim 1, wherein X is —O— or —NR⁷—.

5. A compound according to claim 1, wherein R³ is phenyl substituted with nitro, cyano, amino, halo, hydroxy, C$_{1-4}$alkyloxy, hydroxycarbonyl, aminocarbonyl, mono- or di(C$_{1-4}$ alkyl)aminocarbonyl, C$_{1-4}$alkyloxycarbonyl, C$_{1-4}$alkylcarbonyl, mono- or di(C$_{1-4}$alkyl)methanimidamidyl, N-hydroxy-methanimidamidyl.

6. A compound according to claim 1, wherein each R⁴ or R⁵ independently is hydrogen or C$_{1-4}$alkyl.

7. A compound according to claim 1, wherein each R$^{5a}$ or R$^{5b}$ independently is hydrogen or C$_{1-4}$alkyl.

8. A compound according to claim 1, wherein R⁶ is hydrogen or C$_{1-4}$alkyl.

9. A compound according to claim 1, wherein R⁷ is hydrogen, C$_{1-6}$alkyl optionally substituted with (R⁴)(R⁵)N—, pyrrolidinyl or with piperidinyl.

10. A pharmaceutical composition comprising an effective amount of a compound of formula (I) as defined in claim 1 and a pharmaceutically acceptable carrier.

11. A process for preparing a chemical compound as defined in claim 1, characterized in that a starting material (a) is reacted with an intermediate (b) in an alkylation reaction to yield an intermediate (c), which subsequently is cyclized to yield compounds (I):

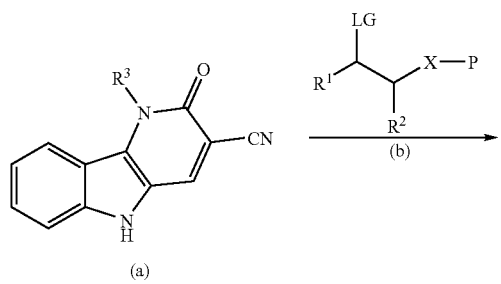

(a)

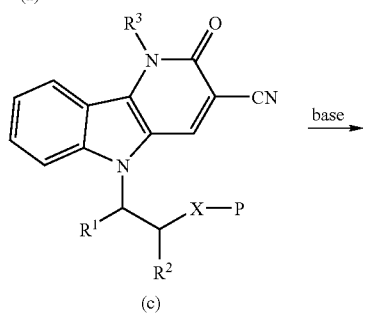

(c)

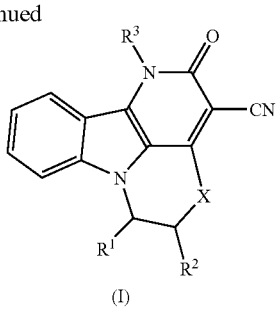

(I)

wherein in the intermediate (b), LG is a leaving group or a leaving group precursor which in situ may be convened into a suitable leaving group, and P is hydrogen or a suitable protecting group; and if desired tranferring the compounds of formula (I) into other compounds of formula (I) with different substitution using functional group transformation procedures; and if desired, preparing salt forms of the compounds of formula (I) by treating the non-salt form with an acid or base.

\* \* \* \* \*